United States Patent
Klemm et al.

(10) Patent No.: US 10,953,157 B2
(45) Date of Patent: Mar. 23, 2021

(54) SENSOR AND SENSOR ASSEMBLY FOR CAPACITIVE DETERMINATION OF A FILLING LEVEL

(71) Applicant: SANOFI-AVENTIS DEUTSCHLAND GMBH, Frankfurt am Main (DE)

(72) Inventors: Thomas Klemm, Frankfurt am Main (DE); Michael Schabbach, Frankfurt am Main (DE); Michael Meindl, Vienna (AT); Robert Lurf, Vienna (AT); Andreas Oberleitner, Vienna (AT); Martin Beisteiner, Vienna (AT)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 329 days.

(21) Appl. No.: 15/566,494

(22) PCT Filed: Apr. 15, 2016

(86) PCT No.: PCT/EP2016/058440
§ 371 (c)(1),
(2) Date: Oct. 13, 2017

(87) PCT Pub. No.: WO2016/166338
PCT Pub. Date: Oct. 20, 2016

(65) Prior Publication Data
US 2018/0093042 A1 Apr. 5, 2018

(30) Foreign Application Priority Data
Apr. 16, 2015 (EP) .................................. 15163896

(51) Int. Cl.
*A61M 5/24* (2006.01)
*A61M 5/20* (2006.01)
(Continued)

(52) U.S. Cl.
CPC .................. *A61M 5/24* (2013.01); *A61J 1/22* (2013.01); *A61M 5/20* (2013.01); *G01D 5/2405* (2013.01);
(Continued)

(58) Field of Classification Search
CPC ... A61M 5/24; A61M 5/20; A61J 1/22; G01D 5/2405; G01F 23/265; G01F 23/266
(Continued)

(56) References Cited

U.S. PATENT DOCUMENTS 6,110,148 A 8/2000 Brown et al.
2002/0188259 A1 12/2002 Hickle et al.
(Continued)

FOREIGN PATENT DOCUMENTS

CN 103852135 6/2014
EP 2284849 2/2011
(Continued)

OTHER PUBLICATIONS

International Preliminary Report on Patentability in International Application No. PCT/EP2016/058440, dated Oct. 17, 2017, 6 pages.
(Continued)

*Primary Examiner* — Phillip A Gray
(74) *Attorney, Agent, or Firm* — Fish & Richardson P.C.

(57) ABSTRACT

The present disclosure relates to a sensor for a capacitive determination of a filling level of a cartridge filled with a liquid substance. The sensor comprises a planar flexible foil arrangeable to an outer circumference of a tubular shaped barrel of the cartridge. The foil has at least a sensing zone, a communication zone and at least a first electrode. The foil further comprises least a second electrode located in the sensing zone, a processor electrically connected with the at
(Continued)

least first and second electrodes, and an antenna located in the communication zone. The antenna is electrically connected with the processor.

19 Claims, 7 Drawing Sheets

(51) Int. Cl.
    *A61J 1/22*         (2006.01)
    *G01F 23/26*       (2006.01)
    *G01D 5/24*        (2006.01)
    *A61M 5/145*       (2006.01)
    *A61M 5/168*       (2006.01)
    *G01F 25/00*       (2006.01)

(52) U.S. Cl.
    CPC .......... *G01F 23/265* (2013.01); *G01F 23/266* (2013.01); *G01F 23/268* (2013.01); *A61M 5/1452* (2013.01); *A61M 5/1684* (2013.01); *A61M 2205/3317* (2013.01); *A61M 2205/3389* (2013.01); *G01F 25/0061* (2013.01)

(58) Field of Classification Search
    USPC ........................................................ 604/232
    See application file for complete search history.

(56) References Cited

U.S. PATENT DOCUMENTS

| | | |
|---|---|---|
| 2006/0124740 A1 | 6/2006 | Woodard et al. |
| 2008/0143345 A1* | 6/2008 | Boudaoud .............. G01N 33/22 324/652 |
| 2009/0318876 A1 | 12/2009 | Hansen et al. |
| 2014/0152323 A1 | 6/2014 | Kumar et al. |
| 2015/0268656 A1* | 9/2015 | Bammer ................. A61M 5/24 700/231 |

FOREIGN PATENT DOCUMENTS

| | | |
|---|---|---|
| JP | 2010-66088 | 3/2010 |
| JP | 2013-167651 | 8/2013 |
| JP | 2013-190347 | 9/2013 |
| JP | 2014-238312 | 12/2014 |
| WO | WO 2007/107562 | 9/2007 |
| WO | WO 2013/138830 | 9/2013 |
| WO | WO 2014/052997 | 4/2014 |

OTHER PUBLICATIONS

International Search Report and Written Opinion in International Application No. PCT/EP2016/058440, dated Aug. 8, 2016, 11 pages.

* cited by examiner

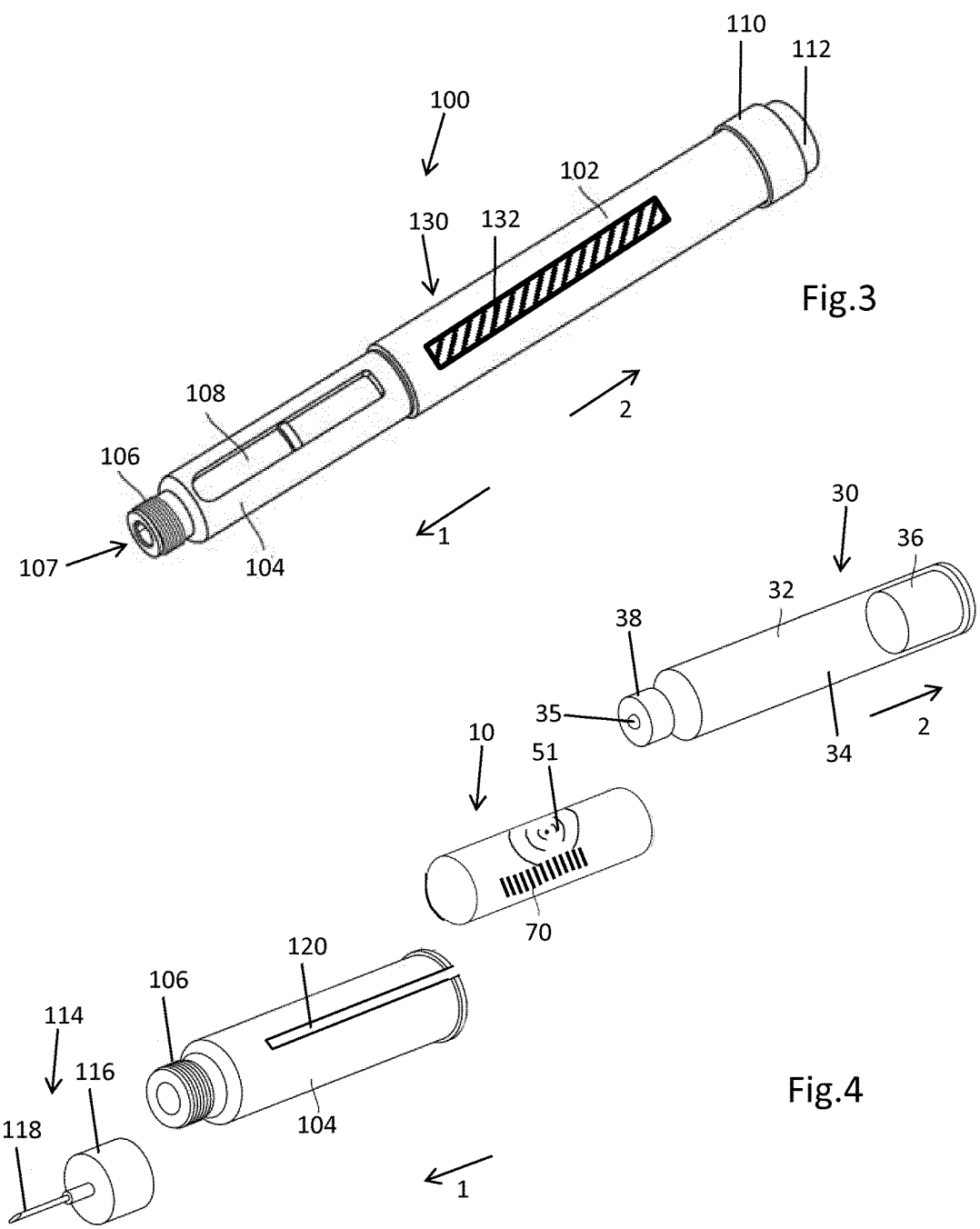

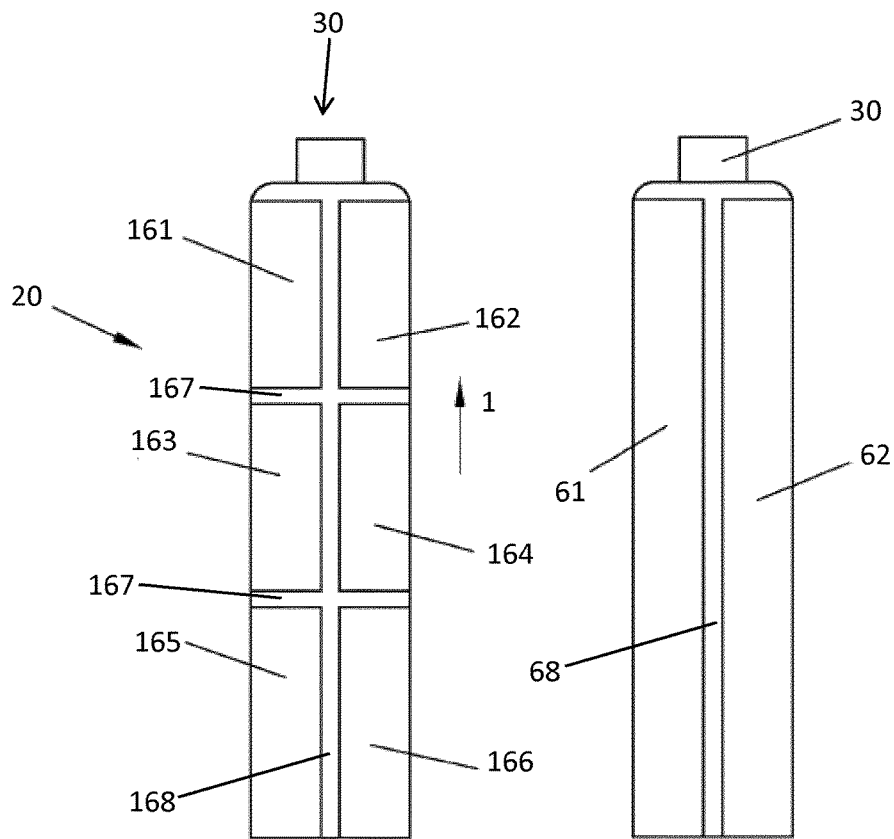
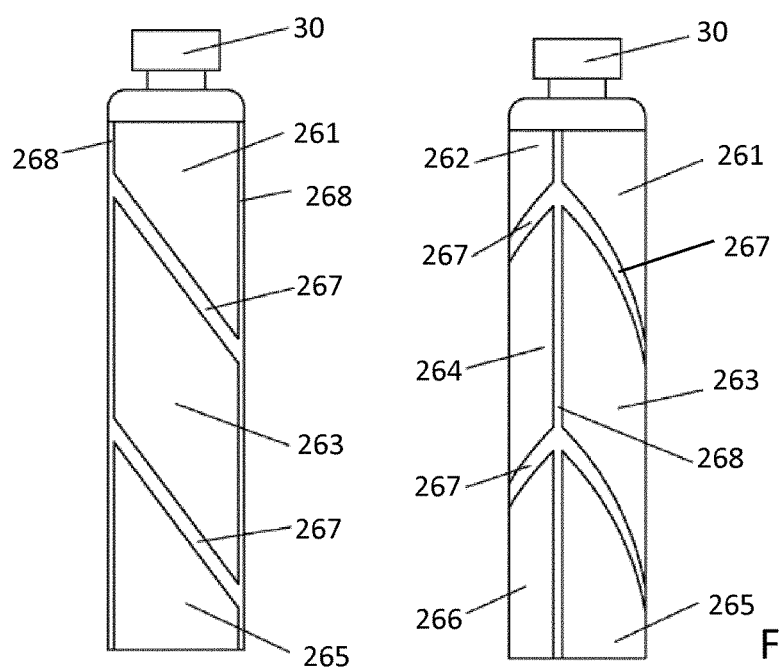

A-A

SENSOR AND SENSOR ASSEMBLY FOR CAPACITIVE DETERMINATION OF A FILLING LEVEL

CROSS REFERENCE TO RELATED APPLICATIONS

This application is a U.S. National stage application under 35 USC § 371 of International Application No. PCT/EP2016/058440, filed on Apr. 15, 2016, which claims priority to European Patent Application No. 15163896.2, filed on Apr. 16, 2015, the entire contents of which are incorporated herein by reference

TECHNICAL FIELD

The present disclosure relates to the field of capacitive determination of a filling level of a cartridge filled with a liquid substance, typically filled with a medicament. In addition, the disclosure relates to a sensor assembly comprising such a sensor fixedly attached to such a cartridge. In a further aspect the disclosure relates to a drug delivery device, in particular to an injection device for setting and dispensing of a dose of a liquid medicament.

BACKGROUND

Drug delivery devices for setting and dispensing a single or multiple doses of a liquid medicament are as such well-known in the art. Generally, such devices have substantially a similar purpose as that of an ordinary syringe.

Drug delivery devices such as pen-type injectors have to meet a number of user-specific requirements. For instance, with patient's suffering chronic diseases, such as diabetes, the patient may be physically infirm and may also have impaired vision. Suitable drug delivery devices especially intended for home medication therefore need to be robust in construction and should be easy to use. Furthermore, manipulation and general handling of the device and its components should be intelligible and easy understandable. Such injection devices should provide setting and subsequent dispensing of a dose of a medicament of variable size. Moreover, a dose setting as well as a dose dispensing procedure must be easy to operate and has to be unambiguous.

Typically, such devices comprise a housing or a particular cartridge holder, adapted to receive a cartridge at least partially filled with the medicament to be dispensed. The device further comprises a drive mechanism, usually having a displaceable piston rod which is adapted to operably engage with a piston of the cartridge. By means of the drive mechanism and its piston rod, the piston of the cartridge is displaceable in a distal or dispensing direction and may therefore expel a predefined amount of the medicament via a piercing assembly, which is to be releasably coupled with a distal end section of the housing of the drug delivery device.

The medicament to be dispensed by the drug delivery device is provided and contained in a multi-dose cartridge. Such cartridges typically comprise a vitreous barrel sealed in distal direction by means of a pierceable seal and being further sealed in proximal direction by the piston. With reusable drug delivery devices an empty cartridge is replaceable by a new one. In contrast to that, drug delivery devices of disposable type are to be entirely discarded when the medicament in the cartridge has been dispensed or used-up.

It is generally desirable to determine the amount of medicament remaining in a cartridge while the cartridge is arranged inside a drug delivery device, such as a pen-shaped injection device. It is generally known in the prior art to implement a capacitive measurement or capacitive determination of a filling level of a cartridge. For this either on the cartridge itself or at the interior of a cartridge holder section of the drug delivery device there are provided at least two electrodes. Since the dielectric properties of the liquid substance inside the cartridge clearly differs from other surrounding materials, such as the vitreous material the cartridge is made of or from the rubber-based material forming the proximal piston of the cartridge, the electrical capacity to be measured between the electrodes located on radially oppositely located sidewall portions of the cartridge correlates with the filling level of the cartridge.

For instance, document WO 2014/052997 A1 discloses a respective dispensing device having at least one pair of capacitive measuring electrodes that are arranged in the outer region of a medicament container, for determining the permittivity of the respective medium in an intermediate region between the measuring electrodes. Furthermore, there is described a shield that is arranged around the container and which surrounds the measurement materials in a sheath-like manner.

The correct arrangement of capacitive electrodes at the outer circumference of such containers is rather delicate and cumbersome. The electrodes must be correctly positioned and arranged relative to the cartridge. Moreover, the electrodes once correctly assembled require electric contacting with a processor in order to provide measurement and data processing of measured capacity values. Only slight modifications or deviations of the relative positioning of at least two electrodes with respect to each other and/or with respect to the cartridge as well as only slight deviations or modifications of the electrical contact with a processor may have drastic consequences on the measurement results. Such high demands in regard to positioning precision and electrical contacting are hardly achievable in a mass manufacturing environment for cartridge- and/or drug delivery device manufacturing.

SUMMARY

Certain aspects provide a sensor for a capacitive determination of a filling level of a cartridge, wherein the cartridge is filled with a liquid substance, typically with a liquid medicament. The sensor comprises a planar flexible foil that is arrangeable at or to an outer circumference of a tubular-shaped barrel of the cartridge. The foil or a foil-like sheet has at least two non-overlapping sections, denoted as a sensing zone and as a communication zone. The sensor further comprises at least a first electrode and a second electrode located in the sensing zone. The electrodes are typically spatially separated from each other in order to allow arrangement of first and second electrodes at radially opposite sections of the sidewall of the cartridge.

The sensor further comprises a processor electrically connected to the at least first and second electrodes. The processor may either be directly or indirectly connected to first and second electrodes. Hence, the first and second electrodes are exclusively electrically connected to a capacity meter, which capacity meter is then electrically connected to the processor. In addition to first and second electrodes and the processor the sensor further comprises an antenna located in the communication zone and being electrically connected to the processor. The antenna may provide a two-fold function. The antenna may provide wireless communication of the sensor with for instance a reader or a further data processing device, such as a smartphone, tablet computer, personal computer or the like. In addition the antenna may be implemented as a radio-frequency identification (RFID) device. It may be implemented as a near-field communication (NFC) device so that the antenna provides wireless coupling with a source of energy in order to provide electrical energy to the processor and/or to the electrodes. By implementing the antenna as an RFID or NFC component the sensor may act like a passive RFID or NFC device that does not require a separate energy source. In this way, the sensor can be void of an own energy source. This enables a low cost and space-saving implementation of such a sensor. Moreover, due to a lack of an own energy source, the overall lifetime of the sensor can be prolonged and no longer depends on the lifetime of the energy source.

First and second electrodes are not only located in the sensing zone but are permanently and fixedly attached to the flexible foil in the region of its sensing zone. In the same way also the antenna is fixedly attached to the foil in the communication zone that is separated from the sensing zone. By having both, the electrodes as well as the antenna attached to one and the same flexible foil, the flexible foil serves as a common support or base of the sensor. Typically, the at least first and second electrodes as well as the antenna are printed or coated on a surface of the flexible foil, which foil is typically electrically insulating. Hence, the foil actually acts as a flexible planar substrate or mechanical support for both the first and second electrodes and the antenna. Implementation of both, the electrodes and the antenna on one and the same flexible foil is beneficial for an assembly process of sensor and cartridge.

When arranging or attaching the sensing zone of the planar flexible foil to the cartridge the antenna is automatically correctly positioned relative to the cartridge. A separate step of antenna assembly and in particular establishing of a mutual electrical interconnection of first and/or second electrodes with the processor and/or with the antenna may then become superfluous. Moreover, having both, namely first and second electrodes printed on or attached to the planar flexible foil the at least two electrodes are inherently correctly positioned relative to each other. During the assembly of the flexible foil and the cartridge, the relative position and/or orientation of the first and second electrodes persists and may only change due to a geometric deformation of the flexible foil.

According to another embodiment, the processor is located in a transition zone of the foil. The transition zone is located between the communication zone and the sensing zone. Typically, the transition zone is sandwiched between the communication zone and the sensing zone. The sensing zone, the transition zone and the communication zone are non-overlapping and all coincide with the planar structure of the foil. While the sensing zone forms a first end, typically a first tangential end of the foil, the communication zone forms an oppositely located tangential end of the foil. As seen in the tangential direction, the transition zone is located between the sensing zone and the communication zone.

The sensing zone and the communication zone are further separated from each other and are interlinked or mechanically interconnected with each other only via the transition zone. Since the planar flexible foil is intended and adapted to be wrapped around the outer circumference of the tubular-shaped barrel the tangential direction denotes the direction of the planar flexible foil along which the foil wraps around the barrel of the cartridge. The planar flexible foil further extends along a further axial direction, which in a final assembly configuration to a cartridge or inside the drug delivery device extends substantially parallel to the longitudinal direction of the cartridge and/or of the drug delivery device. When for instance attached to the outer circumference of the cartridge the at least two electrodes of the sensing zone may be located at radially opposite sides of the cartridge.

When unfolded or when configured in a planar initial shape, the flexible foil may be of substantially rectangular shape, wherein adjacently or neighboring side edges extend at an angle of about 90°, such that one size edge extends in tangential direction and a neighboring or adjacent side edge extends in axial direction. However, the flexible foil may also be of non-rectangular shape. It may have a parallelogram-like or rhombic shape, wherein adjacent side edges are oriented at an angle between 60° and 120°.

The processor is not only located in the transition zone but is also attached or fixed to the flexible foil, hence also fixed to the transition zone. Arranging the processor between the sensing zone and the antenna is of particular benefit for the processing and transmitting of measurement data obtainable from the at least first and second electrodes. Moreover, with such a configuration the electrical energy obtainable via the antenna is modifiable and transferable via the processor in order to provide a suitable driving voltage at the at least first and second electrodes. The arrangement of the processor between the sensing zone and the communication zone also serves to reduce the length of electrical connections between these components thereby enabling and providing a rather robust design and configuration of the sensor.

Moreover, by having arranged first and second electrodes, the processor and the antenna on or in the same planar flexible foil, the mechanically or positionally sensitive components of the sensor are fixed and immobile with regard to each other. In this way, a correct positioning and orientation of electrodes, processor and antenna with respect to each other is highly reproducible and is resistant to eventual modifications in the course of mutual assembly of the sensor and the cartridge.

According to another embodiment, the sensor further comprises an electrical shield located in the communication zone and comprising at least two electrically isolated conductive structures. Typically, the electrical shield extends over the entire communication zone. The electrical shield substantially overlaps with the antenna or completely covers and surrounds the antenna. Typically and in a final assembly configuration the electrical shield is wrapped around the sensing zone so as to serve as a cladding for the sensing zone. In a final assembly configuration in which the flexible foil is wrapped around the tubular barrel of the cartridge the electrical shield is typically radially sandwiched between the communication zone and the sensing zone.

In this way, the sensing zone and hence the rather sensitive electrodes thereof can be effectively protected and shielded against any potential variations of the electromagnetic field in the vicinity of the sensor. Moreover, the electrical shield may serve and act as a kind of approach sensor or touch sensor by way of which approaching of e.g. an object, such as a finger in the direct vicinity of the sensor can be detected. In this way, the electrical shield not only serves to protect first and second electrodes against EMI emissions but also provides an effective means to compensate or to counteract any detrimental effects of the arrangement of first and second electrodes in response to an approaching of an object that may modify the dielectric properties in the sensor's vicinity.

According to another embodiment, the electrical shield and the antenna are electrically isolated and are further located on opposite sides of the flexible foil. Since the flexible foil is electrically insulating a simple arrangement of antenna and electrical shield on opposite sides, e.g. on an upper side and on a lower side of the flexible foil inherently provides a sufficient electrical insulation therebetween. Moreover, in a final assembly configuration, in which the communication zone is wrapped around the outer circumference of the tubular-shaped cartridge, the antenna, typically located on an outside facing portion of the foil, is radially separated from the electrical shield at an inside facing portion of the wrapped or coiled flexible foil.

According to another embodiment, the foil is substantially transparent. The foil typically comprises or is made of a transparent polymer. The foil may comprise at least one or a combination of the materials polycarbonate, polyimid, or polyvinyl chloride (PVC). Moreover, the foil is printable or coatable with electrically conductive structures, such as with at least first and second electrodes, the antenna or the electrical shield. Moreover, first and second electrodes, processor, antenna as well as electrical shield may be electrically connected by means of several conducting paths that may be simultaneously printed or coated onto the foil. The conducting paths may be of the same material as the antenna, the shield and/or the electrodes. Typically, at least one of the antenna, the shield, the first or second electrodes and the conducting path comprise a metallic and conducting material or even consist of such an electrically conductive material.

By having arranged all electrical components of the sensor on one and the same planar flexible foil, mechanical interfaces, such as plugs or other connectors between the sensor's electrical components become superfluous. Due to the transparent foil and/or the transparent electrodes, conducting path, shield or antenna, the interior of e.g. the vitreous cartridge is still visually inspectable. The electronic components of the sensor, i.e. first and second electrodes, the antenna or the shield may comprise or may consist of indium-tin oxide (ITO) that is conductive and substantially transparent. Alternatively, the electronic components may comprise or consist of a comparable electrically conductive and transparent material.

Thanks to the transparent foil and/or the transparent electronic structures attached thereto or embedded therein the content of the transparent and vitreous cartridge remains visually inspectable. Visual inspectability of the interior of the cartridge is of particular importance in order to provide an intuitive control whether the content of the cartridge, in particular the liquid medicament might be subject to coagulation or flocculation or some other detrimental effects or phenomena.

According to another embodiment, the sensor comprises a visual scale in the communication zone. The visual scale may be persistently printed on an upper side or lower side of the flexible foil in the communication zone. The scale may comprise various symbols, numbers or other signs in order to visually display a momentary filling level of the cartridge. Typically, the scale comprises numerous equidistantly arranged scale items that are typically separated along the axial direction of the flexible foil. The scale items are typically printed on the flexible foil and comprise a color that is non-transparent and distinguishes from the visual appearance of the electronic components of the sensor.

By implementing a visual scale in or on the foil of the sensor providing of a comparable scale in a cartridge holder of a drug delivery device may become superfluous. With the arrangement or attachment of the sensor's flexible foil to the outer circumference of the cartridge the cartridge itself is inherently provided with a visual scale thereby providing a very intuitive and straightforward approach to determine a filling level of the liquid substance inside the cartridge. It is only necessary to arrange the flexible foil at a predefined orientation and predefined position to the outer circumference of the tubular barrel of the cartridge.

In some embodiments the flexible foil and/or the visual scale completely covers the outer circumference, hence the outer sidewall of the cartridge. The cartridge typically comprises a radially narrowed neck or head portion near its distal end, which in proximal direction widens to the tubular or cylindrically-shaped barrel of the cartridge. In typical embodiments the flexible foil and/or the scale provided thereon completely cover the cylindrical or tubular-shaped portion of the barrel of the cartridge in axial as well as in tangential direction.

The visual scale may be of further use to indicate or to visualize the position of the antenna. This may be of particular use for a mutual arrangement of the antenna and a corresponding reader, e.g. for sensor powering and/or data acquisition.

According to a further embodiment, the sensor comprises a temperature sensor in one of the communication zone, transition zone or sensing zone. The temperature sensor might be integrated into the processor and may be arranged in the transition zone. Alternatively, the temperature sensor may be provided on or in the sensing zone and may be connected via a separate conducting path with the processor. In any case the temperature sensor might get in direct contact with the outer circumference of the barrel of the cartridge thereby allowing a rather direct measurement of the temperature of the liquid substance contained in the cartridge. Injection of a cold liquid substance may lead to discomfort of a patient. By sensing or determining the temperature of the liquid substance or liquid medicament the processor might be further implemented to provide an alert or a similar warning that is either visually, haptically or audibly communicated to the patient thereby indicating that the actual temperature of the liquid substance is below a predefined threshold.

The temperature sensor may be implemented as a separate integrated circuit printed on a predefined portion of the flexible foil and being electrically connected to the processor by means of at least one conducting path. Alternatively, the temperature sensor may be directly integrated into the processor to achieve an even higher level of integration and to reduce the cost of sensor assembly and sensor manufacturing.

According to a further embodiment, the sensor also comprises a capacity meter that is electrically connected with the first and with the second electrode. The capacity meter may comprise an integrated circuit and may be operable to provide the at least two electrodes with a driving voltage. It may be further operable to determine the electrical capacity between the at least two electrodes. When provided as a separate component the capacity meter is typically arranged rather symmetric with regard to first and second electrodes. It is typically arranged in the sensing zone. For reasons of symmetry it may be positioned midway between first and second electrodes in regard to both, the tangential direction as well as in regard to the axial direction. By means of the capacity meter first and second electrodes are electrically connected to the processor.

The capacity meter is integrated into the processor so that a separate implementation of a capacity meter in the sensing zone becomes superfluous. By implementing the capacity meter into the processor, an even higher degree of integration of the sensor can be attained, thus allowing a reduction in manufacturing and assembly costs.

In a further embodiment, the transition zone of the flexible foil comprises a narrowed neck portion formed by at least one lateral recess in a side edge of the foil. Typically, two oppositely located side edges of the flexible foil exhibit rather symmetric lateral recesses in order to form a lateral and narrowed neck portion in the transition zone. The lateral recesses extend in axial direction of the foil. The recess or narrowed neck portion of the transition zone is not only beneficial to save material but is of particular benefit for arranging the cartridge connected with the sensing zone of the flexible foil into a correspondingly-shaped cartridge holder of the drug delivery device.

It is particularly intended to wrap the flexible foil in a two-fold manner around the outer circumference of the cartridge. Typically, the sensing zone forms a first loop or wrap and is directly connectable across its entire surface with the outer circumference of the cartridge's sidewall whereas the communication zone is wrappable around a sleeve-shaped cartridge holder accommodating the cartridge with the sensing zone. The transition zone located between the sensing zone and the communication zone may then extend through a slit or a gap in the sidewall of the cartridge holder so that the communication zone is wrappable around the outer circumference of the tubular or sleeve-shaped cartridge holder while the sensing zone is directly fixed to the cartridge. By reducing the axial dimensions of the transition zone of the flexible foil and by implementing an axially narrowed neck portion insertion of the neck portion or transition zone into a longitudinal slit of the cartridge holder becomes rather simple and straightforward. A danger of damaging the flexible foil, in particular its transition zone during insertion of the cartridge into the cartridge holder can therefore be reduced.

According to another embodiment, the first and the second electrodes are tangentially separated, extend substantially parallel and comprise a tapered structure in an axial distal direction. The geometric shape of the electrodes might be trapezoidal, triangular or a may comprises a combination of a rectangular and a triangular shape. By using electrodes having a geometric structure changing constantly in axial direction, a respective linearly changing capacity signal is obtainable as the piston of the cartridge is subject to a linear axial displacement. The shape of the electrodes may thereby improve the accuracy and precision of the capacity measurement.

In some embodiments, the sensing zone comprises not only a first and a second, hence a first pair of first and second electrodes but that the sensing zone is provided with several pairs of first and second electrodes. In a further embodiment, a pair of first and second electrodes may be arranged tangentially separated in a common axial region of the sensing zone while at least a second pair of first and second electrodes being tangentially separated may be arranged axially adjacent to the first pair of first and second electrodes, and so on. Typically, each pair of electrodes is separately electrically connected with the processor or with a capacity meter. The pairs of adjacent pairs of electrodes are separated in axial direction so that an axial resolution of the capacity-based determination of the position of the cartridge's piston can be improved.

Alternative to a tapered structure the electrodes may also comprise a rectangular, triangular, trapezoidal, rhombic, diamond-like or parallelogram-like structure. The first and second electrodes of a pair of electrodes comprise comb-like structures that are arranged in a mutually meshing configuration. The axial dimensions of first and second electrodes may correspond to the axial dimension of the cartridge's piston. The axial dimension of the first or second electrode may be substantially identical to the axial elongation of the piston.

The filling level of the cartridge is typically determined on the basis of a measurement of the capacity between a pair of first and second electrodes. An electrical capacity measured by the electrodes being in direct contact with the outer circumference of the barrel of the cartridge is typically compared with a calibration table or look-up table providing an assignment of capacities with filling levels in accordance with a previously conducted calibration procedure.

In some embodiments, the sensor comprises at least one additional capacity measuring electrode by way of which external effects are detectable that may have a detrimental influence on the capacity measurement. In case that a capacity measurement dedicated to external effects, such as approaching of external objects or EMI sensitive influences, should display a capacity above a predefined threshold, a measured capacity between the pair of first and second electrodes could be discarded. In this way, it can be generally checked whether the filling level as determined by means of the capacity measurement of first and second electrodes, has been influenced or distorted, e.g. by touching of the electrodes or by approaching of an external object, such as a human finger or the like in close vicinity to the electrodes.

Furthermore, for a precise determination of the filling level. the actual measured signals reflecting the filling level and/or an estimation about the validity of the actually measured filling level can be transferred to external communication devices, such as mobile phones, tablet computers or smartphones via encoded electromagnetic data transmission, in particular based on load modulation.

Furthermore, for a precise detection and determination of the filling level it is beneficial, when:
a) for a number of filling levels there are provided reference vectors that include capacities between the pairs of first and second electrodes as components, and
b) assigning to each of these vectors a corresponding filling level inside the cartridge,
c) determining of a vector including the single determined capacities,
d) forming of an interpolation function, providing a respective filling level when applied to the reference vectors according to step b), and
e) the interpolation function is applied to this vector, wherein the result is used as the actual filling level.

According to another embodiment, the processor of the sensor is arranged on a rigid printed circuit board that is fixed to or which is integrated into the foil. The printed circuit board may be located in the transition zone of the foil or may form or constitute the transition zone. The printed circuit board is typically connected to the foil all over its surface or along its outer circumference. Hence, the printed circuit board, which is of planar shape, extends coplanar or parallel to the planar flexible foil.

Typically, a lower surface of the printed circuit board facing away from the processor is for example adhesively attached to the flexible foil over its entire lower surface. In this way, the transition zone of the foil is somewhat stiffened and may become substantially inflexible. The printed circuit board may extend all over the transition zone, e.g. from a proximal longitudinal end of the foil to a distal longitudinal end of the foil. In lateral or tangential direction the printed circuit board may be confined by the sensing zone and by the communication zone.

By means of the rigid printed circuit board the rather sensitive and fragile sensor can be handled appropriately. Hence, the printed circuit board provides a gripping structure or gripping means to enable and to simplify the mechanical handling thereof, in particular in a mass manufacturing environment. Furthermore, by having a rigid printed circuit board the electronic components located thereon and fixed thereto can be inherently protected against mechanical impact. In addition, the printed circuit board provides a mount for the mutual assembly of sensor, cartridge and/or a distal housing component of a drug delivery device.

Another aspect relates to a sensor assembly for a capacitive determination of a filling level of a cartridge, typically filled with a liquid medicament. The sensor assembly comprises a sensor as described above. The sensor, in particular its flexible foil is wrapped to form an inner wrap and to form an outer wrap. Typically, inner and outer wrap of the flexible foil are arranged in a nested or convoluted way. Hence, the inner wrap is at least partially or completely enclosed by the outer wrap. Inner and outer wraps are aligned coaxially, i.e. respective central axes of inner wrap and outer wrap extend substantially parallel or even coincide.

The flexible foil is coiled or wrapped so that the sensing zone thereof is located in the region of the inner wrap and that the communication zone of the foil is located in the outer wrap. In the sensing zone first and second electrodes forming a first pair of electrodes are arranged at such a lateral distance so that when wrapped or coiled around the outer circumference of the cartridge's barrel first and second electrodes are substantially geometrically radially opposed on the outer circumference of the barrel.

In this way, the first and the second electrodes are operable to determine an electric capacity therebetween, hence, inside the cartridge. The sensor assembly further comprises at least one of a cartridge and a cartridge holder. The cartridge has a tubular-shaped barrel and is filled with a liquid substance, typically with a liquid medicament. The cartridge holder is typically also of tubular shape to accommodate the cartridge. The cartridge holder may belong to a housing of an injection device. The cartridge holder typically serves to fix and to mechanically support the cartridge inside the housing of the injection device.

The sensor, in particular its foil is attached to the cartridge or to the cartridge holder. The sensor, in particular the foil of the sensor is attached to both, the cartridge and to the cartridge holder.

In one embodiment, the sensor assembly essentially consists of the sensor attached to the cartridge, thereby forming a cartridge preassembly. In such a configuration the sensor does not need to be manually connected or attached to the cartridge. In particular, the sensor, at least the sensing zone thereof, may be adhesively attached to the outer circumference of the cartridge. Hence, a cartridge manufactured and delivered by a pharmaceutical manufacturer can be readily equipped with a filling level determining sensor. Such an embodiment is particularly useful for disposable injection or drug delivery devices.

In another embodiment, the sensor is attached to the cartridge holder but is disconnected from the cartridge to be arranged therein. Such an embodiment is of particular use where the injection device or drug delivery device is implemented as a reusable device, allowing and providing frequent replacement of an empty cartridge. When exclusively attached to the cartridge holder the sensing zone of the sensor might be arranged along the inside of a sidewall of the cartridge holder so that the cartridge can be arranged and inserted in axial direction radially inside the inner wrap. If the cartridge should be empty it can be replaced by a new one without the necessity to disassemble the sensor and the cartridge holder.

According to another embodiment, the sensing zone on or in the inner wrap of the sensor's foil, is wrapped around the outer circumference of the barrel and is adhesively attached to the barrel. In this way, the first and second electrodes are arranged at radially opposite sidewall portions of the barrel. The foil, at least sensing zone of the foil, is then typically adhesively attached across its entire surface with the outer circumference of the cartridge's barrel. Moreover, the tangential and/or axial size of the sensing zone matches with the entire outer circumference of at least the cylindrical portion of the cartridge's barrel so as to completely wrap the barrel. By means of covering the complete outer circumference of the vitreous cartridge, typically made of glass, also an effective splinter shield is given for the cartridge in the event that the cartridge should become subject to breakage. Since the entire outer circumference of the cartridge is adhesively bonded with the planar flexible foil a spreading of eventual splinters of fragments of a broken cartridge barrel can be effectively prevented. This does not only increase patient safety but also improves the quality standard of fully automated cartridge handling and cartridge assembly in a mass manufacturing environment.

According to a further embodiment, the cartridge holder of the sensor assembly is substantially sleeve-shaped or tubular shaped and is optionally to be assembled into a distal housing component of a drug delivery device. The cartridge holder is configured to accommodate the cartridge and has a longitudinal slit in a sidewall portion through which the flexible foil extends. Typically, it is the transition zone and/or the printed circuit board that radially extends through said longitudinal slit. The longitudinal slit is typically open in axial proximal direction so that a cartridge equipped with the sensor, i.e. having the sensing zone adhesively attached to its outer circumference is insertable from a proximal end of the cartridge holder towards the distal end thereof. The longitudinal slit of the cartridge holder's sidewall portion allows an axial insertion of the transition zone in distal direction so that in a subsequent step of assembly the communication zone of the foil is wrappable around the cartridge holder or an inner sleeve, respectively. In this way, the sensor, with the flexible foil, is wrappable in a two-fold manner around the cartridge.

Typically, the inner wrap of the sensor is wrappable around or is actually wrapped around the outer circumference of the cartridge whereas the communication zone, hence the outer wrap of the sensor is wrappable around the outer circumference of the cartridge holder. In an intermediate or end assembly configuration, the inner wrap and the outer wrap are separated in radial direction by means of the tubular-shaped sidewall of the cartridge holder. The communication zone can be adhesively attached to the outer circumference of the cartridge holder but may be also fixed to the cartridge holder in a different way. Arranging the sensing zone around the cartridge and arranging the communication zone with the antenna around the outer circumference of the cartridge holder, provides an electrical insulation between the radially overlapping sensing zone and communication zone. Moreover, the axial and tangential dimensions of the communication zone typically match with the tangential and axial circumference of the cartridge holder or inner sleeve. In this way, the outer wrap formed by the communication zone of the foil completely covers the outer circumference of the cartridge holder.

Consequently, when the electrical shield completely covers the communication zone the electrical shield also inherently covers and shields the entirety of the sensing zone located radially beneath. By arranging the flexible foil in a two-fold manner around the cartridge, namely by forming an inner wrap and an outer wrap, a well-defined relative positioning of electrodes, antenna and electrical shield can be obtained. By means of the flexible foil separately fastened and attached to the cartridge holder and the cartridge, respectively, the cartridge can be mechanically fixed to the cartridge holder, which is beneficial in the process of fully automated assembly of the drug-delivery device. The sensor assembly including the cartridge and the cartridge holder forms a pre-assembly unit in which the cartridge is secured against unintentional separation from the cartridge holder. Thus, the sensor assembly may flip over in the course of manufacturing and assembling of the drug delivery device without the cartridge separating from the cartridge holder.

With the two-fold wrapping, a configuration is attainable, wherein the first and second electrodes are located at a radially innermost position, while the antenna is located at a radially outermost position. Arranging of the first and second electrodes directly at the outer circumference of the cartridge is beneficial for a precise measurement of the capacity. Arranging the antenna radially outwardly, typically at an outside facing surface of the outer wrap is beneficial for wireless data transmission and electrical energy transfer.

The two-fold wrapping of the cartridge is also beneficial in order to provide mechanical protection of the processor arranged in the transition zone. In an embodiment the outer wrap may completely cover the processor. The outer cover or wrap may further provide a rather even and smooth outer surface of the sensor assembly. Moreover, the outer shield covers the processor so that also the processor is effectively protected against eventual EMI noise.

According to a further embodiment, the processor and/or the printed circuit board is located inside the slit of the cartridge holder or inner sleeve, respectively. The processor or the printed circuit board may comprise a thickness larger than the thickness of further electronic components of the sensor, such as the first and the second electrodes, the antenna or the electrical shield. Typically, the processor comprises a thickness that is smaller than the thickness of the sidewall portion of the cartridge holder. By arranging the processor inside the slit of the cartridge holder the processor is mechanically protected when located inside the slit. In addition, the processor can be covered by the outer wrap formed by the communication zone of the flexible foil. In this way, the processor can even be encapsulated inside the slit. It may be radially inwardly encapsulated by the foil's transition zone. It may be radially outwardly encapsulated by the communication zone of the flexible foil and it may be tangentially encapsulated by the slit of the cartridge holder's sidewall portion. The slit therefore forms a radial recess in the sidewall structure of the cartridge holder that is configured to completely receive and to completely accommodate the processor.

Since the processor is received inside the slit, a radial gap size between the outer surface of the cartridge's barrel and the interior surface of the cartridge holder can be reduced to a minimum. In particular, the radial gap size may be smaller than the radial thickness of the processor.

According to another embodiment, the inner wrap is arranged or attached to an inside of the sidewall portion of the cartridge holder. Here, the foil of the sensor may be entirely or completely fixed exclusively to the cartridge holder. The inner wrap is attached to the inside of the sidewall of the cartridge holder whereas the outer wrap is attached to the outer circumference of the sidewall of the cartridge holder. By exclusively fixing the sensor to the cartridge holder there is no direct mechanical connection required between the cartridge and the sensor as the cartridge is located inside the cartridge holder.

Typically, the inner diameter or inner cross section of the cartridge holder substantially matches with the cross section of the cartridge so that the cartridge located inside the cartridge holder is positioned between at least two electrodes that are located radially opposite with the tubular-shaped cartridge sandwiched there between. A configuration of the sensor assembly wherein the sensor is exclusively fixed or attached to the cartridge holder is of particular use when the respective drug delivery device or injection device is configured as a reusable device.

Since the cartridge may be slidably arranged inside the cartridge holder, and hence inside the inner wrap of the sensor, it may be exchanged by longitudinally directed sliding, during which the displacement of the cartridge is relative to the cartridge holder or sensor. The inner wrap may be fixed to the inside of the sidewall of the cartridge holder by friction or by means of some fixing means, such as an adhesive or other mutually corresponding fixing elements.

In some embodiments, the flexible foil is resiliently deformable so that at least one of inner or outer wrap tends to unfold into a rather planar shape. In this way, the inner wrap may inherently tend to unwrap or to unfold when assembled inside the cartridge holder. Due to such a resilient deformable behavior, the inner wrap clings to the inside of the cartridge holder's sidewall. Similarly the outer wrap has a tendency to unfold or to unwrap. In this case, it is of particular benefit that the assembly of sensor and cartridge holder is arranged inside a distal housing component of the respective drug delivery device.

Then, the outer wrap or communication zone of the sensor may snugly engage or cling to the interior of the distal housing component's sidewall. In this way, the radial distance or separation of inner and outer wrap may increase. Moreover, at least one of inner and outer wraps adapts to the inside facing sidewall portions of cartridge holder or distal housing component, respectively. Due to the inherent elasticity of the planar flexible foil the accessible inner diameter of the cartridge holder can be automatically maximized for receiving the cartridge. Due to the elasticity and the resilient behaviour of the flexible foil it is in principle not necessary to attach the inner or the outer wrap to the cartridge holder. It may be sufficient when cartridge holder and sensor are mutually attached via the processor or via the printed circuit board. In this way, the printed circuit board or the processor not only provides electrical signal processing but also serves as a support or a means for a mutual assembling of cartridge holder and sensor.

In a further embodiment, the electrodes of the sensing zone are located on an inside facing side of the inner wrap and the antenna of the communication zone is located on an outside facing side of the outer wrap. When the inner wrap and outer wrap are coiled around the cartridge and the cartridge holder, the electrodes and the antenna are located on opposite sides of the flexible foil. Since the electrical shield is located on an opposite side with regard to the antenna it follows that the electrical shield and the electrodes are located on the same side of the flexible foil. In this way, the electrical shield is facing radially inwardly and is attached to the outer circumference of the cartridge holder whereas the antenna faces radially outwardly and is provided on a radially outwardly facing side of the flexible foil of the sensor. The electrodes face radially inwardly and are in direct contact with the outer circumference of the cartridge.

In this way, the arrangement of the at least first and second electrodes is effectively electrically shielded but the antenna of the sensor is located radially outside of the electrical shield so that data transmission and energy supply is substantially unaffected by the electrical shield.

In another embodiment of the sensor assembly, the printed circuit board of the sensor and the cartridge holder comprise mutually engageable fastening elements for a mutual fixing of sensor and cartridge holder. The sensor and the printed circuit board may each comprise at least one fastening element. Mutually corresponding or mutually engageable fastening elements of sensor and printed circuit board may be of positively engaging, frictionally engaging or adhesively engaging type.

The fastening elements of the sensor and the printed circuit board comprise mutually corresponding clip features that provide a releasable or non-releasable mutual fastening of sensor and cartridge holder. For example, the printed circuit board may comprise a recess or a through opening into which or through which a complementary-shaped fastening pin of the cartridge holder may extend.

In this way, a mutual fixing and attachment of the sensor and the cartridge holder can be obtained via the rigid printed circuit board. This provides a rather precise and robust mutual interconnection of sensor and cartridge holder. By fixing the cartridge holder and the sensor through the printed circuit board, an easy and intuitive assembly process can be obtained.

The mechanical rigidity of the printed circuit board allows and provides well-defined handling of the sensor during the assembly process with the cartridge holder or for the assembly of the sensor inside the housing of a drug delivery device.

Another aspect relates to a drug-delivery device for setting and for dispensing of a dose of a medicament. The drug-delivery device is typically implemented as an injection device, e.g. as a pen-type injector of elongated shape. The drug delivery device comprises a housing to accommodate a drive mechanism and to accommodate a cartridge filled with a liquid medicament. The drive mechanism typically comprises a piston rod that is displaceable in an axial distal direction to exert distally directed thrust to a piston of a cartridge. In this way, a predefined amount of the liquid medicament can be expelled through a distal outlet of the cartridge typically in fluid communication with an injection needle. By means of the piston rod the fluid pressure inside the cartridge is increasable so that a predefined amount of the medicament is expelled from the interior of the cartridge.

The drug-delivery device further comprises a sensor assembly as described above by way of which a filling level of the cartridge is measurable or determinable. Due to the antenna of the sensor, the sensor or the sensor assembly does not require any electrical or further mechanical interconnection or interaction with the drug delivery device. Moreover, since the sensor is implemented as an RFID or NFC device, the drug delivery device does not have to provide a power supply for the sensor to function. Thus, existing designs of drug delivery devices may be easily retrofitted with a sensor and with a sensor assembly as described above. Power supply and data communication with the sensor may be implemented by an external electronic device, such as a particular wireless reader, smartphone, tablet computer or personal computer equipped with a respective communication protocol.

Alternatively, a wireless reader to interact with the sensor is implemented in the drug delivery device so that information about the actual filling level may be provided to a user of the device through the drug delivery device.

In the present context, the distal direction points in the direction of the dispensing and of the device, where typically a needle assembly is provided having a double-tipped injection needle that is to be inserted into biological tissue or into the skin of a patient for delivery of the medicament.

The proximal end or proximal direction denotes the end of the device or a component thereof, which is furthest away from the dispensing end. Typically, an actuating member is located at the proximal end of the drug delivery device, which is directly operable by a user. The drug delivery device is configured to be rotated to set a dose and is configured to be depressed in distal direction to dispense of a dose.

According to a further embodiment, the drug delivery device comprises a sensor with a rigid printed circuit board and the drug delivery device further comprises a distal housing to accommodate the sensor assembly. The distal housing further comprises at least one fastening element to engage with a correspondingly-shaped fastening structure or with a correspondingly-shaped fastening element of the printed circuit board of the sensor assembly. In this way, and by means of mutually corresponding fastening elements or fastening structures of the distal housing and the printed circuit board, the sensor or the sensor assembly, consisting of sensor and cartridge or cartridge holder, may be fixed to the distal housing via the printed circuit board.

The fastening structure of the printed circuit board may be integrated or may be formed by the outer circumference or by the outer edges of the planar-shaped printed circuit board. Accordingly, the fastening element of the distal housing may be configured as or may comprise clamping members or a frame to receive the fastening structure of the printed circuit board and to fix the printed circuit board to the distal housing by means of a positive or frictional engagement.

In this way, the cartridge holder is fixed to the distal housing of the drug delivery device through the printed circuit board of the sensor or of the sensor assembly. Fastening elements of the printed circuit board and of the distal housing substantially overlap so that one fastening element of the cartridge holder engages with both, the fastening element of the printed circuit board and with a complementary-shaped fastening element on the interior or inside the distal housing.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein In a further embodiment, the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein In a further embodiment, the pharmaceutically active compound comprises at least one peptide for the treatment and/or prophylaxis of diabetes mellitus or complications associated with diabetes mellitus such as diabetic retinopathy, wherein In a further embodiment, the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28]Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28]Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys) 6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three on the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from the spirit and scope of the invention. Further, it is to be noted, that any reference numerals used in the appended claims are not to be construed as limiting the scope of the invention.

Some embodiments may advantageously provide a sensor for a capacitive determination of a filling level of a cartridge that allows for an easy and reproducible assembly to or relative to the cartridge and which is further beneficial in terms of electrical contacting during the assembly and manufacturing process of a cartridge and/or of a respective drug delivery device or injection device. Some embodiments may further provide a highly integrated, low cost and mass manufacturing suitable sensor and sensor assembly for a capacitive determination of a cartridge's filling level. Some embodiments provide a sensor or sensor assembly to provide capacitive determination of a filling level of a cartridge to be replaceable assembled in an injection device or drug delivery device. The sensor or sensor assembly may be suitable for use with disposable injection devices as well as with reusable drug delivery devices.

BRIEF DESCRIPTION OF THE DRAWINGS

In the following, an embodiment of the display arrangement, the drive mechanism and the drug delivery device is described in detail by making reference to the drawings, in which:

FIG. 3 is a perspective schematic view of a drug delivery device, FIG. 4 is an exploded view of components of the drug delivery device, FIG. 5 schematically shows an arrangement of three pairs of electrodes axially separated along the longitudinal axis of the cartridge, FIG. 6 shows an embodiment with only two axially elongated electrodes, FIG. 7a shows an embodiment with three pairs of electrodes of rhombic or parallelogram-like shape in a first orientation, FIG. 7b shows the embodiment according to FIG. 7a in another orientation of the cartridge.

DETAILED DESCRIPTION

Figure 1:
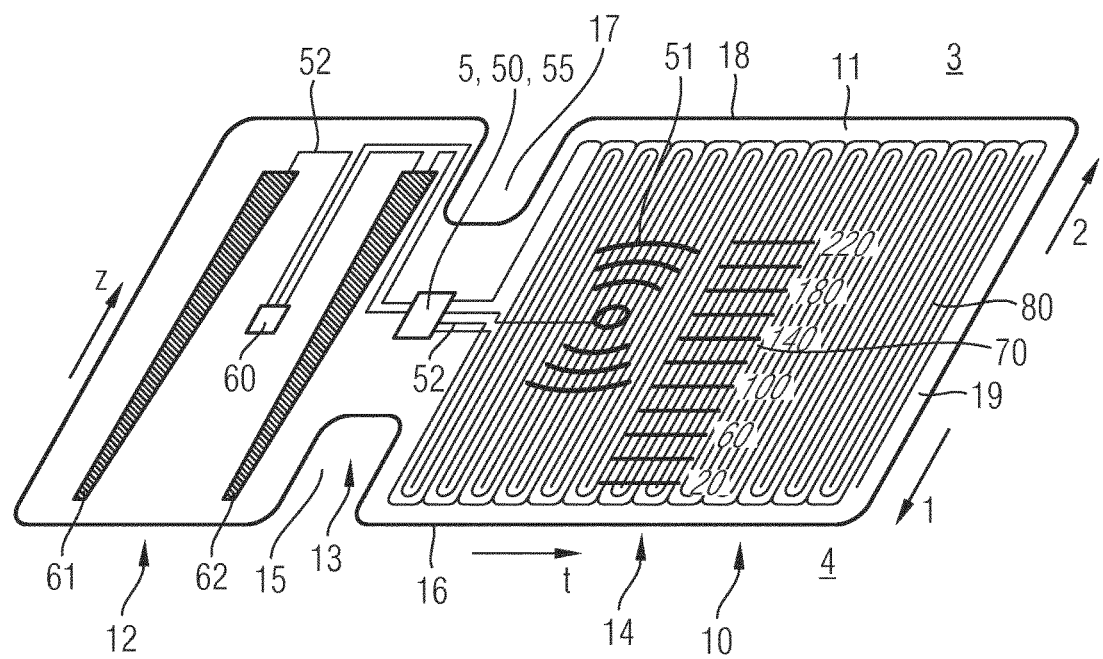
FIG. 1 is a schematic view of the sensor in a planar and initial configuration prior to an assembly to the cartridge.
Figure 2:
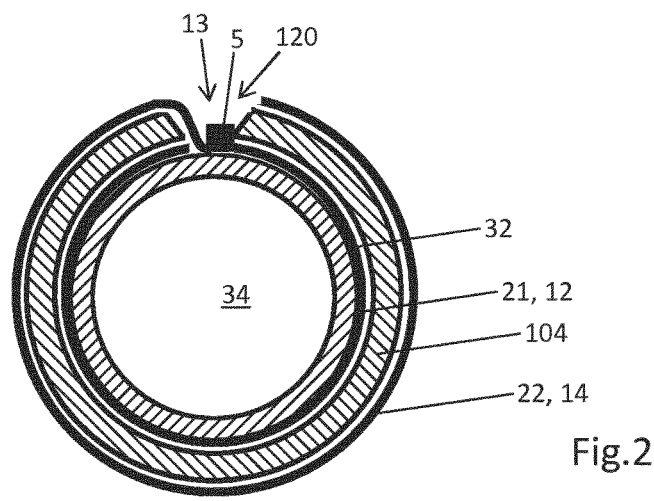
FIG. 2 is a cross section of a sensor assembly, wherein the sensor and its flexible foil is wrapped around the cartridge and the cartridge holder by forming an inner wrap and an outer wrap, respectively.

The sensor 10 as illustrated in a planar and initial configuration in FIG. 1 comprises a planar and flexible foil 11 that serves as a substrate to which various electronic components of the sensor 10 are attached. The foil 11 of the sensor is imaginary separated in three non-overlapping adjacent zones. As shown in FIG. 1, the foil 11 comprises a sensing zone 12 forming one tangential end of the foil 11, a transition zone 13 and a communication zone 14, wherein the communication zone 14 forms an opposite tangential end of the foil 11. The foil 11 is intended to be coiled or to form an at least two-fold wrap as illustrated in FIG. 2. Therefore, the substantially rectangular or planar shaped foil 11 extends in two directions, namely in a tangential direction, that is horizontal in the illustration according to FIG. 1 and in an axial direction oriented substantially vertical in the perspective illustration according to FIG. 1. When in an assembly configuration as shown in FIG. 2 the axial direction (z) of the foil 11 is parallel to the longitudinal direction of the tubular-shaped cartridge 30 and/or of the sleeve-shaped cartridge holder 104. Accordingly, a lower end of the flexible foil 11 as shown in FIG. 1 points in distal direction 1 whereas an upper end of the flexible foil 11 points in proximal direction 2.

The flexible foil 11 is substantially transparent and is adhesively attachable at least to the outer circumference of the cartridge 30. The sensing zone 12 of the sensor 10 is provided with at least one pair of electrodes 61, 62. As shown in FIG. 1, the first and the second electrodes 61, 62 are electrically connected to a capacity meter 60 that is located midway between the electrodes 61, 62. The electrodes 61, 62 extend substantially parallel and exhibit an elongated shape extending in axial direction (z). The capacity meter 60 is connected with the electrodes 61, 62 by means of printed conducting paths 52. Also the electrodes 61, 62 are typically printed onto the top side 3 or upper surface of the foil 11. When attached to the barrel 32 of the cartridge 30 the top side 3 of the foil 11 points radially inwardly and gets in direct mechanical contact with the outer circumference of the barrel's 32 sidewall. In this way, first and second electrodes 61, 62 get in direct mechanical contact with the sidewall of the barrel 32 of the cartridge 30. Typically, the foil 11, at least in its sensing zone 12 is provided with an adhesive completely covering the sensing zone 12 with the exception of the electrodes 61, 62. In this way, a rather homogeneous and durable mutual fixing of the foil 11 and the cartridge 30 can be obtained.

The substantially rectangular-shaped sensing zone 12 adjoins the transition zone 13 in tangential direction (t). The transition zone 13 contains a processor 50 that is at least electrically connected with the capacity meter 60 by means of conducting paths 52. In an alternative embodiment, the capacity meter 60 may be directly integrated into the processor 50. The processor 50 is then electrically connected with both, first and second electrodes 61, 62.

The transition zone 13 features an axially narrowed neck portion. The axial extension of the transition zone 13 is smaller compared to the axial extension of the sensing zone 12. It may be also smaller than the axial extension of the communication zone 14 that adjoins the transition zone 13 in tangential direction. Typically, the axial extension of sensing zone 12 and communication zone 14 are substantially equal. In this way, sensing zone 12 as well as communication zone comprise a substantially rectangular shape. Apart from the axially narrowed transition zone 13 the foil 11 has a rather rectangular shape with two oppositely located side edges 16, 18 that confine the axial extension of the foil 11. The axially narrowed transition zone 13 is located midway between the oppositely located axial side edges 16, 18. The transition zone 13 may be formed by axial recesses 15, 17 in the respective side edges 16, 18. The axially narrowed transition zone 13 is of particular benefit when it comes to the assembly of the sensor 10 to the cartridge 30 and cartridge holder 104 as will be explained below.

In or on the communication zone 14, an antenna 51 is electrically connected to the processor 50 by means of printed conducting paths 52. By means of the antenna 51, the processor 50 is capable of communicating with external electronic devices in a wireless way. Consequently, the antenna 51 may be designed as an RFID antenna or NFC antenna. The antenna 51 not only provides wireless data transmission between the processor 50 and an external device, but may also provide electrical energy to the processor 50 as well as to the electrodes 61, 62. The antenna 51 may be also implemented as a printed or coated conducting structure on a surface of the flexible foil 11.

In the communication zone 14 a visual scale 70 is further provided, comprising numerous scale items that are equidistantly separated in axial direction (z). The scale 70 typically comprises a visual structure and the scale items comprise a color that differs from the color or visual appearance of the antenna 51. The scale 70 is of particular use when the flexible foil 11 and the cartridge holder 104 are substantially transparent. In this way, the content of the transparent cartridge 30 located underneath is visually inspectable. The scale 70 attached to the cartridge holder 104 is then directly indicative of the filling level of the liquid substance inside the cartridge 30.

Figure 10:
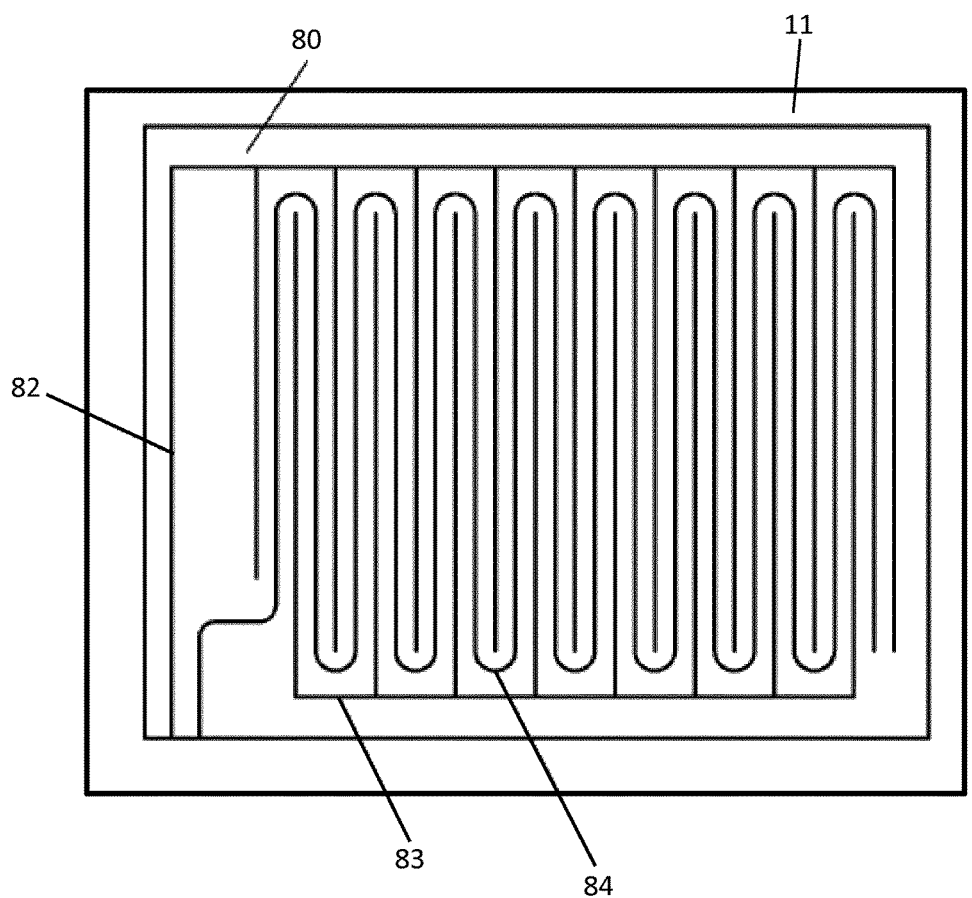
FIG. 10 is a schematic illustration of an electrical shield.

In addition to the antenna 51, the communication zone 14 is further provided with an electrical shield 80. The electrical shield 80 comprises numerous separated conductors or conductive structures extending over the surface of the communication zone 14. The conductors 82, 83, 84 of the electrical shield 80 as illustrated in FIG. 10 serve to shield the electrodes 61, 62 against external influences, such as EMI noise or against other detrimental effects that may arise when e.g. objects that may have an impact on the capacity measurement are approaching the sensor. The antenna 51 and the electrical shield 80 are located on opposite sides of the foil 11. In this way, the antenna 51 and the electrical shield 80 are electrically isolated or insulated by the foil 11.

The electrical shield 80 may be also electrically connected to the processor 50. Moreover, the electrical shield 80 may further act as a touch or approaching sensor. Signals obtainable from the electrical shield 80 may therefore be processed in order to discard an actual capacity measurement because the actual capacity measured by means of the electrodes 61, 62 may have been influenced by an external object, such as a finger of a person in the direct vicinity to or in mechanical contact with the sensor 10.

Arrangement of all electrical components of the sensor 10 on a single and common foil 11 is of particular benefit since eventual electrical or mechanical interconnections between e.g. the electrodes 61, 62, the processor 50, the antenna 51 or the electrical shield 80 become superfluous. Moreover, it is intended that all electrically conducting structures of the sensor 10, namely the electrodes 61, 62, the conducting paths 52, the antenna 51 as well as the electrical shield 80 are attached to the flexible foil 11 by way of printing or by way of coating. The position and relative orientation of these electronic components or conductive structures is therefore fixed. It remains substantially unaffected during assembly of the sensor to the cartridge 30 and/or to the cartridge holder 104. By making use of printed or coated conductive structures on the flexible foil 11 a large number of substantially identical sensors are producible 10 at low costs.

The sensor 10 as illustrated in FIG. 1 is designed for assembly to a cartridge 30 and to a cartridge holder 104 of a drug delivery device. A typical drug delivery device 100 is shown in FIG. 3. The drug delivery device 100 is implemented as an injection device, in particular as a pen-type injector. The injection device or drug delivery device 100 comprises a proximal housing 102 also denoted as body that accommodates a drive mechanism 130. The drive mechanism 130 comprises at least an axially extending piston rod 132 that is displaceable in distal direction 1 and which is adapted to exert distally directed pressure to a piston 36 of a cartridge 30 as illustrated in FIG. 4.

The axial advancing of the piston rod 132 is controllable by a dose setting and dispensing mechanism of the drive mechanism 130. Typically, the drug delivery device 100 comprises a dose dial 110 as well as a dose button 112 at its proximal end. By means of the dose dial 110, a dose of the medicament of variable size can be set. Thereafter and through depression of the dose button 112 the piston rod 132 advances in distal direction 1 in accordance with the size of the previously set dose. The cartridge 30 as illustrated in FIG. 4 comprises a tubular-shaped or cylindrically-shaped barrel 32 filled with a liquid medicament 34. In proximal direction 2, the cartridge is sealed by a piston 36. The piston 36 is displaceable inside the cartridge 30 in distal direction 1.

The distal end of the cartridge 30 comprises a distal seal 35 that is penetrable by double-tipped injection needle 118 of a needle assembly 114. The distal seal 35, typically implemented as a pierceable septum is kept in position at a stepped down neck portion or distal head of the cartridge 30 by means of a closure 38, typically comprising a crimped aluminium cap. The cartridge 30 is assembled inside a tubular-shaped cartridge holder 104, which may form the distal end of the drug delivery device 100. In the illustration according to FIG. 3, the cartridge holder 104 is substantially non-transparent but comprises an inspection window 108 through which the content of the transparent cartridge 30 is visually inspectable. The cartridge holder 104 further comprises a threaded socket 106 at its distal end featuring a through opening 107 to receive the distally directed pointed tip of the injection needle 118. The injection needle is fixed to a needle hub 116 of sleeve-shaped geometry. The inside-facing sidewall portion of the needle hub 116 comprises an inner thread, by which the needle hub 116 is threadedly engageable with the threaded socket 106 of the cartridge holder 104. In this way, the needle assembly 114 can be mounted to the cartridge holder 104 and a fluid communication between the injection needle 118 and the interior of the cartridge 30 can be established.

The cartridge holder 104 as illustrated in FIG. 4 is typically transparent and comprises a longitudinal slit in the sidewall. The longitudinal slit 120 is open towards the proximal direction 2. FIG. 4 further illustrates the sensor 10 in a coiled or wrapped configuration and the antenna 51. Tangentially adjacent to the antenna 51, the visual scale 70 provides a direct and intuitive filling level determination. The visual scale 70 can be viewed and compared against the contents of the barrel 32 due to the transparency of the transparent cartridge holder 104, the transparent foil 11, the transparent barrel 32 and the substantially transparent electrical shield 80 of the sensor 10.

The sensor 10 is wrapped around the convoluted or nested arrangement of cartridge 30 and cartridge holder 104. In a preassembly configuration or in a first step of assembly the flexible foil 11, in particular the sensing zone 12 of the foil 11, is wrapped around the outer circumference of the sidewall of the cylindrical portion of the barrel 32 of the cartridge 30. Typically, the sensing zone 12 is adhesively attached across its entire surface with the outer circumference of the barrel 32 so as to form a first or an inner wrap 21 completely covering the outer circumference of the tubular portion of the barrel 32. In this preassembly configuration, the arrangement of sensor 10 and cartridge 30 is insertable from a proximal end into the cartridge holder 104 along the distal direction 1, wherein the transition zone 13 of the foil 11 extends radially outwardly so as to allow insertion thereof through and into the longitudinal slit 120.

In some embodiments, the transition zone 13 comprises at least a recess 15 in distal direction 1 so as to limit the axial size of the slit 120. The axially narrowed transition zone 13 is further of benefit since a rather narrow transition zone 13 in axial direction (z) is less sensitive to mechanical damage upon insertion of sensor 10 and cartridge 30 into the cartridge holder 104. In addition, by means of the distally facing recess 15, the overall axial length of the slit 120 can be reduced and a mechanical stability of the cartridge holder 104 can be improved. Hence, the distal end of the cartridge holder 104 is slit-free.

Once the cartridge 30 together with the sensor 10 reaches a final assembly configuration inside the cartridge holder 104 the foil 11 is wrappable around the outer circumference of the cartridge holder 104 with its communication zone 14. The communication zone 14 may also be adhesively attached to the outer circumference of the cartridge holder 104. As illustrated in FIG. 2, the processor 50 is located in the transition zone 13 so that the processor 50 is located inside the longitudinal slit 120 of the cartridge holder 104. In this way, the processor 50, which may be implemented as in integrated circuit 5, is mechanically protected by the sidewall of the cartridge holder 104. By means of the adhesively attachable sensor 10, the cartridge 30 is also axially fixable inside and relative to the cartridge holder 104.

In the illustration according to FIG. 2 the communication zone 14 forms a second or outer wrap 22. The antenna 51 is typically located on a radially outside facing portion of the communication zone 14, whereas the electrical shield 80 is facing radially inwardly, towards the radially outwardly facing surface of the sidewall of the cartridge holder 104. In this way, electrical energy supply, as well as wireless data transmission provided by the antenna 51, is not affected by the electrical shield 80.

In the embodiment illustrated in FIG. 2 the outer wrap 22 ends at the slit 120 and does not cover the slit in order to avoid an eventual electrical contact of the electrical shield 80. However, in some embodiments, the foil 11 in the communication zone 14 is not completely covered by the electrical shield 80, but the foil 11 comprises a lateral boundary portion 19 as shown in FIG. 1 that is free of any electrically conductive structures. With an electrically insulating boundary portion 19, the outer wrap 22 completely encloses the outer circumference of the cartridge holder 104. Hence, the outer wrap 22 may also completely cover the axial slit 120. In this way, the slit 120 is protected against ingress of particles or humidity. Moreover, the mechanical structure of the cartridge holder 104 can be stabilized through an adhesive connection with the communication zone 14 of the foil 11 extending over the slit 120. When the outer wrap 22 completely covers the outer circumference of the cartridge holder 104, the cartridge holder 104 obtains a rather smooth and even shaped outer appearance.

It is to be noted, that the communication zone 14 is not necessarily attached to a cartridge holder 104. Likewise, it is connectable and wrappable around an inner separate sleeve of the sensor assembly 20 or of the drug delivery device 100. The inner separate sleeve, with the cartridge 30 mounted therein, is to be assembled into a separate cartridge holder 104, for example as illustrated in FIG. 3.

The sensor 10 as illustrated in FIG. 1 may be further equipped with a temperature sensor 55, which in the present embodiment is integrated into the processor 50. Since the processor 50 is directly arranged adjacent or on the outer surface of the cartridge 30 a thermal coupling of temperature sensor 55 and cartridge 30 is obtained. By means of the temperature sensor 55, the actual temperature of the cartridge 30, in particular of the liquid contents 34 of the cartridge 30, is determinable. When the temperature is below a predefined threshold, the processor 50 may communicate this temperature information to an external electronic device via the antenna 51, thereby indicating to the user, that injection of the liquid medicament may cause discomfort.

It is further apparent from FIG. 1, that the two electrodes, namely first and second electrode 61, 62 display a tapered and narrowing structure in axial distal direction 1. In this way, an even larger and continuous variation of the capacity between the electrodes 61, 62 is measurable as the piston 36 of the cartridge 30 advances in distal direction 1.

Figure 8:
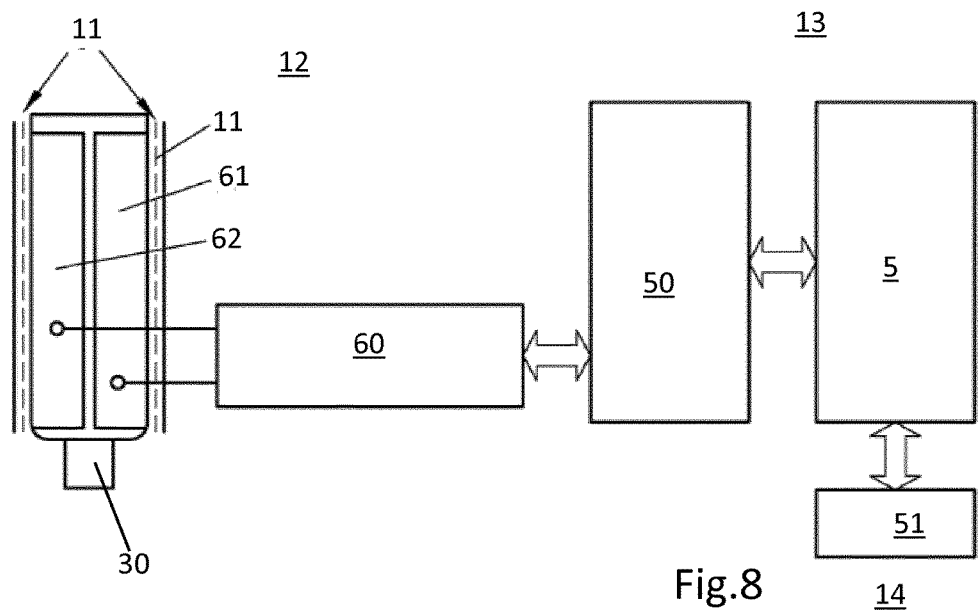
FIG. 8 shows a block diagram of the electronic components of the sensor with only two electrodes.

FIG. 6 shows an alternative embodiment of the electrode design of the sensor 10. The tangential size of the first and second electrodes 61, 62 is increased compared to the embodiment as shown in FIG. 1. The electrodes 61, 62 each cover almost one half of the outer circumference of the cartridge 30 when attached thereto. The axial elongation of the electrodes 61, 62 matches and substantially coincides with the axial extension of the tubular portion of the barrel 32 of the cartridge 30. In tangential direction, the first and second electrodes 61, 62 are separated by an elongated gap 68 extending in axial direction. As indicated in the block diagram according to FIG. 8, each one of the electrodes 61, 62 is separately connected to the capacity meter 60, which is further electrically connected to the processor 50. The processor 50 may be integrated into an integrated circuit 5 or may be designed itself as an integrated circuit 5. Hence, the processor 50 and the integrated circuit 5 may also coincide and may not be realized as separate units.

The processor 50, typically implemented as a microcontroller, is furthermore electrically connected to the antenna 51. Depending on the filling level of the cartridge 30, the measurable capacity between the radially geometrically opposite electrodes 61, 62 varies. The capacity meter 60, which may be also implemented as an integrated circuit or as a microcontroller is configured to transmit measured capacity data to the processor 50 so as to calculate the filling level on the basis of the measured capacity. The calculated filling level may then be transmitted to an electronic device via the antenna 51. Alternatively, it is also conceivable that calculation of the filling level is conducted by an external device adapted to communicate with the sensor 10 via the antenna 51 of the sensor 10. The processor 50 is configured to transmit and to broadcast the actual measured capacity values provided by the first and second electrodes 61, 62.

In FIG. 5 another arrangement of three pairs of electrodes, namely a first pair of electrodes 161, 162 a second pair of electrodes 163, 164 and a third pair of electrodes 165, 166, is illustrated. The pairs of electrodes are axially separated by means of two tangentially extending gaps 167. Electrodes of a pair of electrodes are separated by two axial gaps 168 as indicated in FIG. 5.

Figure 9:
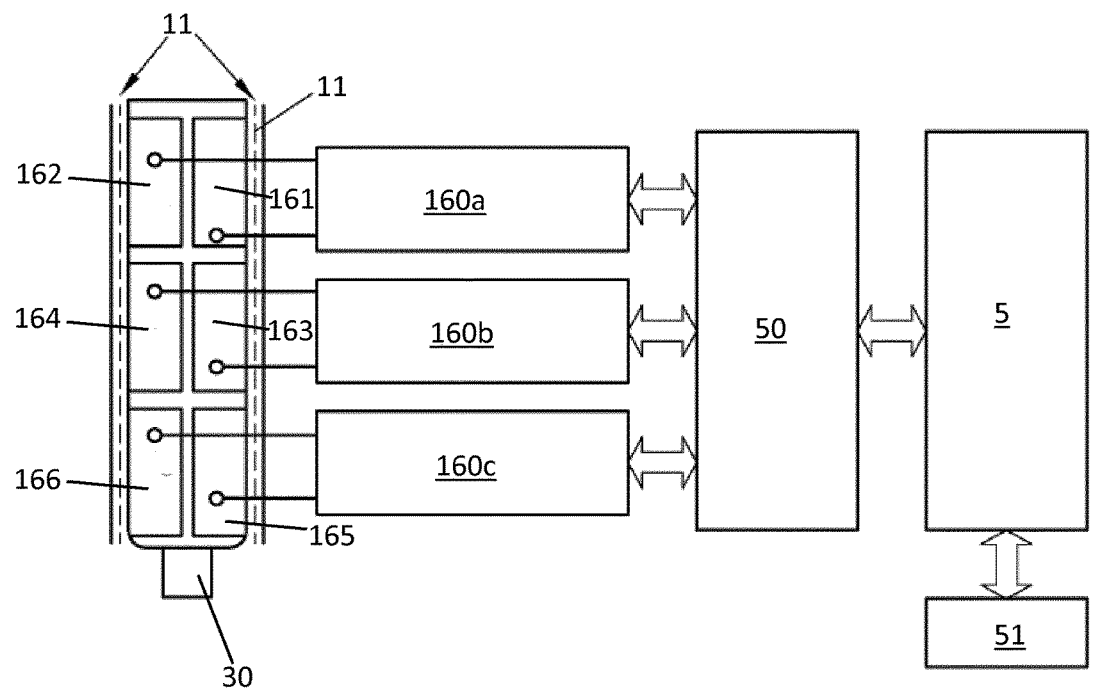
FIG. 9 shows another block diagram of the sensor with three pairs of electrodes attached to the outer circumference of the cartridge.

With three pairs of electrodes, three different capacities of three adjacent axial portions of the cartridge 30 are measurable. As further shown in FIG. 9, each pair of electrodes 161, 162, 163, 164, 165, 166 is connected to a separate capacity meter 160a, 160b and 160c. Hence, the capacity meter 160a measures the capacity of the first pair of electrodes 161, 162, the capacity meter 160b measures the capacity of the second pair of electrodes 163, 164 and the third capacity meter 160c measures the capacity between the third pair of electrodes 165, 166. As the piston 36 is moved in distal direction 1 in the course of subsequent dose dispensing or dose injecting procedures, typically one or two of the pairs of electrodes 161, 162, 163, 164, 165, 166 are subject to a change of capacity. With several pairs of electrodes, the precision of filling level detection or filling level determination can be enhanced. As illustrated in FIG. 9, the separate capacity meters 160a, 160b, 160c are electrically connected with the processor 50. By processing measurement data of the three capacity meters 160a, 160b, 160c, precise fill levels can be determined.

For instance, in addition to the absolute values of the capacities, the sum of capacity values of the capacity meters 160a, 160b, 160c may be used as a criterion for filling level determination.

As shown in FIGS. 7a and 7b some embodiments implement a number of pairs of electrodes of rhombic, parallelogram-like or even comb-like shape. In the example of rhombic or parallelogram shape electrodes 261, 262, 263, 264, 265, 266 as shown in FIGS. 7a and 7b, those electrodes form a first, second and third pair of electrodes, namely electrodes 261, 262, electrodes 263, 264 and electrodes 265, 266 and are separated by an axially extending gap 268. However, neighboring pairs of electrodes that are located axially adjacent are separated by a gap 267 extending at an angle smaller than 90° with respect to the axial direction. The slope or slanted orientation of the gap 267 between pairs of electrodes provides a smooth transition of measured capacities as the piston 36 moves from an axial position, substantially overlapping with a first pair of electrodes, towards a second axial position, in which the piston 36 substantially overlaps exclusively with a second pair of electrodes.

Since the separation of axially adjacently located pairs of electrodes extends at a predefined angle, for instance at about 45° with respect to the tangential and/or axial direction, changes in capacity measurements conducted by a first and a second pair of electrodes become smooth.

According to an alternative solution, the electrodes may comprise a comb-like or meander-like structures that mutually mesh. Such electrode structures could provide an improved accuracy of capacity measurement and filling level determination.

Hence, the first and second electrodes 61, 62 may comprise a structure that is similar to the structure of the comb-like conductors 82, 83 of the electrical shield 80, as schematically shown in FIG. 10.

The electrical shield 80 and the antenna 51 are located on opposite sides of the foil 11. In this way, the electrical shield 80 is provided on the interior surface of the second wrap 22 of the coiled elastic foil 11. The antenna 51 is provided on the radial outside facing surface of the foil 11 when coiled to the outer wrap 22. In the embodiment according to FIG. 2, the two wraps 21, 22 are coiled in the same direction, the electrodes 61, 62 are arranged on the same side of the foil 11 as the electric shield 80 and the antenna 51 is located on an opposite side of the foil 11.

In an alternative embodiment to the configuration according to FIG. 2, the coiling directions of the inner wrap 21 and the outer wrap 22 are substantially opposite. Hence, the sense of coiling of the outer wrap 22 is opposite to the sense of coiling of the inner wrap 22. In such an embodiment, the transition zone 13 would be folded around a longitudinal edge of the longitudinal slit 120 formed by the sidewall portion of the cartridge holder 140. In such a configuration, the antenna 51 and the electrodes 61, are arranged on the same side of the foil 11, while the electric shield 80 is provided on an opposite side of the foil 11.

The electric shield as illustrated in FIG. 10 comprises three conductive structures, a first conductor 82, a second conductor 83 and a third conductor 84. The first and second conductors 82, 83 exhibit a comb-like structure and mutually mesh with comb teeth of the first conductors 82 with comb teeth of the second conductor 83 in an electrically isolated but spatially overlapping way. The third conductor 84 has a meander-like structure and extends between the comb teeth of the comb structures of first and second conductors 82, 83.

The conductors 82, 83, 84 are arranged on the flexible and insulating foil 11 by coating or printing. Typically, the conductors 82, 83, 84 feature a thickness of about 50 µm. They may have a width of about 1 mm. Preferably, the width of the conductors 82, 83, 84 is between 100 µm and 3 mm.

In order to suppress eddy currents that could have a negative impact on RFID or NFC-communication, the width of the conductors 82, 83, 84 is typically less than 3 mm. Moreover, the conductors 82, 83, 84 are free of any electric loops. In this way, any negative impacts due to RFID or NFC-communication can be effectively suppressed while simultaneously screening or shielding the sensitive measurement conducted by the electrodes 61, 62.

The electrical shield 80 as illustrated in FIG. 10 may also act as an approaching or touch sensor. The first comb-like conductor 82 and the meander-shaped third conductor 84 act as a touch sensor while the second conductor 83 is connected to ground and serves as an electric shield. In the event that a person approaches the sensor 10 or the electric shield 80 or the electric shield 80 is touched, e.g. by a finger of a person, the permittivity of the environment of the conductors 82, 84 is measurably changed. A separate capacity meter, which is not explicitly illustrated, detects this change in capacity. By providing such a capacity change to the processor 50, the additional detected and modified capacity of the electrical shield 80 can serve as an indicator that the measurement conducted by the electrodes 61, 62 in contact with the cartridge 30 may have been externally influenced.

For instance, if the capacity change detected by the electrical shield 80 is above a predefined threshold, the actual capacity measurement conducted by the first and second electrodes 61, 62 can be discarded. Alternatively or additionally, it is conceivable that a respective alert is generated by the processor 50 and that a respective alert is displayed or otherwise indicated by an electronic device that is in wireless communication with the sensor 10.

Figure 11:
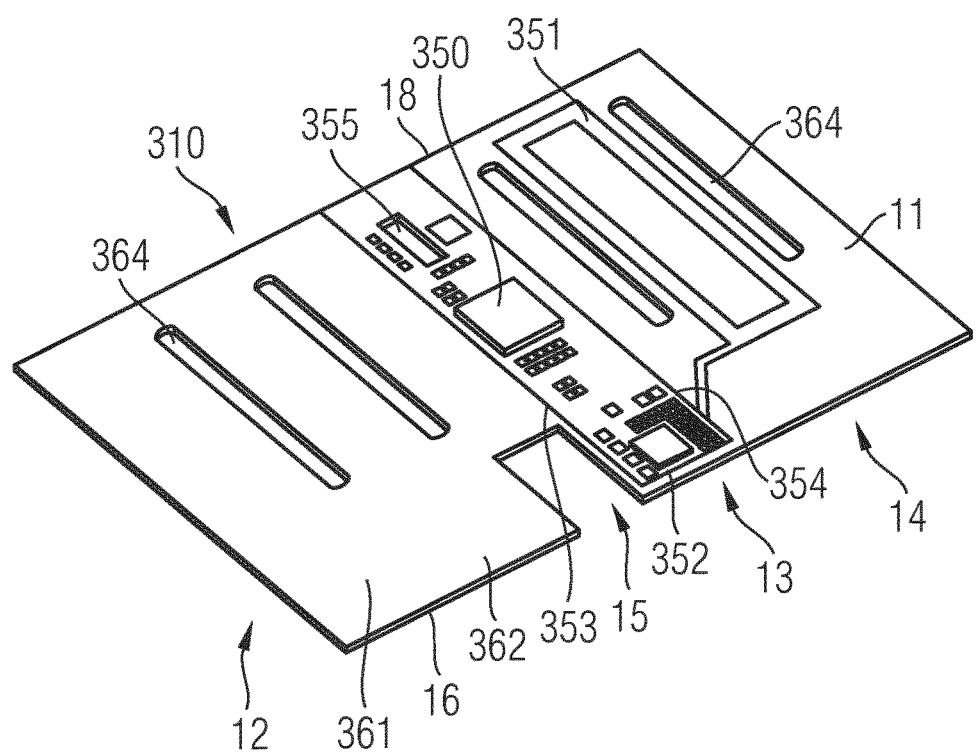
FIG. 11 shows another embodiment of the sensor with a rigid printed circuit board.
Figure 12:
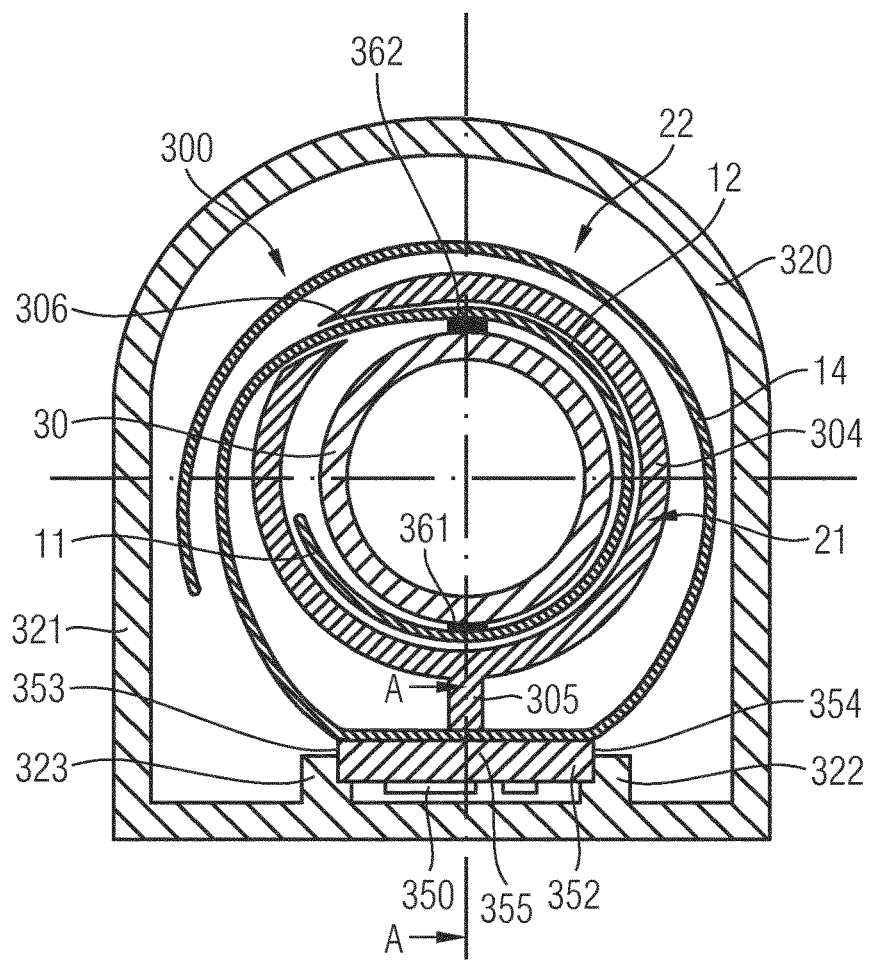
FIG. 12 is illustrative of a transverse cross section through the drug delivery device.
Figure 13:
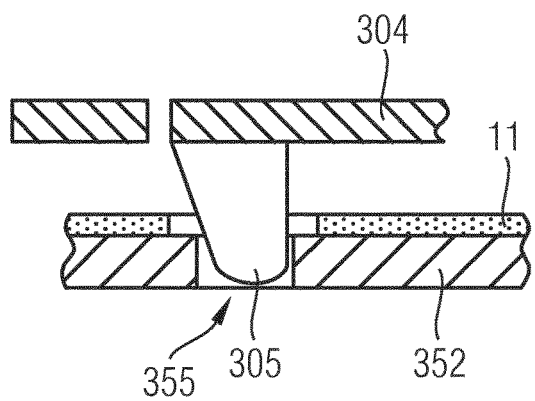
FIG. 13 is a cross section along A-A according to FIG. 12.

The further embodiment of a sensor 310, a sensor assembly 300 and a drug delivery device as shown in FIGS. 11-13 is substantially equivalent or identical to the sensor 10, the sensor assembly 20 and the drug delivery device 100 as described above unless described otherwise. The sensor 310 as shown in a planar configuration according to FIG. 11 also comprises a flexible and initially planar foil 11 that is divided into a sensing zone 12, a transition zone 13 and a communication zone 14. In the sensing zone 12 there are provided two longitudinally or axially extending electrodes 361, 362 that extend substantially parallel.

The electrodes 361, 362 are separated in tangential direction, i.e. perpendicular to their longitudinal extension in such a way that when arranged around the outer circumference of a cartridge 30, as shown in FIG. 12, the electrodes 361, 362 are located on geometrically opposite sidewall portions of the cartridge 30. As further illustrated in FIG. 11, the communication zone 14 is provided with an antenna 351. The sensor 310 may be further equipped with a shield as described in connection with the sensor 10 according to FIG. 1. However, in FIG. 11 this shield is not explicitly illustrated.

In the transition zone 13 located between the sensing zone 12 and the communication zone 14, a rigid printed circuit board 252 is provided. The printed circuit board 352 comprises at least one processor 350 that is electrically connected with the electrodes 361, 362 and the antenna 351. The printed circuit board 352 may be adhesively connected with the foil 11. As shown in FIG. 11, the rigid printed circuit board 352 extends over the entire longitudinal extension of the transition zone 13. Furthermore, the printed circuit board 352 comprises at least one fastening element 355.

The fastening element 355 may comprise a through opening or a recess in the rigid substrate of the printed circuit board 352. The fastening element 355 engages with a correspondingly-shaped fastening element 305 of the cartridge holder 304. In this way, cartridge holder 304 and printed circuit board 352 can be mutually interconnected by means of correspondingly-shaped fastening elements 305, 355. The cartridge holder 304 is almost identical to the cartridge holder 104 as described in connection with the sensor 10 and sensor arrangement 20.

The cartridge holder 304 is also of tubular shape and comprises a longitudinal slit 306 in a sidewall portion 308. The flexible foil 11 coiled in form of an inner wrap 21 and an outer wrap 22 radially extends through said slit 306. The fastening element 305 of the cartridge holder 304 may radially outwardly protrude from the tubular-shaped sidewall 308 of the cartridge holder 304. The fastening element 305 can be configured as a fastening pin or a fastening clip that frictionally or positively engages with the correspondingly-shaped fastening element 355 of the printed circuit board 352.

As further shown in FIGS. 11 and 12, the printed circuit board 352 comprises two oppositely located longitudinally extending side edges 353, 354. The side edge 353 faces towards the sensing zone 12 whereas the oppositely located side edge 354 faces towards the communication zone 14. The side edges 353, 354 are configured as fastening structures of which the printed circuit board 352 of the sensor 310 or sensor assembly 300 can be fixed and attached to the interior or the distal housing 320 of the drug delivery device.

Hence, the distal housing 320 comprises a sidewall 321 having fastening elements 322, 323 to engage with correspondingly-shaped fastening structures 354, 353 of the printed circuit board 352. In this way, the printed circuit board 352 may be releasably fastened to the interior of the distal housing 320 by simply clipping or clamping the rigid printed circuit board 352 into the recessed structure formed by the fastening elements 322, 323 of the distal housing 320.

In this way, the printed circuit board 352 can be rigidly fastened to the distal housing 320 and/or to the cartridge holder 304. The rigid structure of the printed circuit board 352 mechanically protects the rather sensitive electronic components, such as the processor 350, against mechanical impact that may otherwise arise due to bending of the foil 11.

In the embodiment shown in FIGS. 11-13, the assembly of the sensor 310 and the cartridge holder 304 is exclusively obtained via the mutually engaged fastening elements 305, 355. In this way, it is not necessary to adhesively attach the foil 11 to the cartridge holder 304 or to the cartridge 30. The inner wrap 21 may be simple obtained due to the resilient or elastic properties of the initially planar flexible foil 11. The foil 11 may have a tendency to relax into its initial planar state as shown in FIG. 11.

When assembled inside the tubular-shaped cartridge holder 304 the inner wrap 21, hence the sensing zone 12, may frictionally engage or may simply tend to expand radially outwardly, thereby clinging to the inside of the sidewall 308 of the cartridge holder 304. In a similar way also the outer wrap 22 located radially between the outer circumference of the cartridge holder 304 and the inside of the distal housing 320 may equally adapt to the shape and may hence expand to adhere or to cling to the inside of the sidewall 321 of the distal housing 320.

With the combination of fixing of the sensor 310 and the cartridge holder 304 in mutual attachment, providing a mutual assembly and fixing of the sensor 310 with the distal housing 320, it is no longer necessary to permanently attach the cartridge 30 to the foil 11 of the sensor 310. The cartridge 30 located inside the sensor assembly 300 formed by the cartridge holder 304 and the sensor 310 is easily replaceable or interchangeable, simply by way of a longitudinal sliding relative to the cartridge holder 304. In this way, the sensor assembly 300 is configured to be used with reusable drug delivery devices 100 that provides replacement of an empty cartridge and a reset operation of the drive mechanism.

In order to modify or to control the resilient behaviour of the foil 11, various longitudinally extending recesses or slits 364 enable a well-defined or predefined bending of the foil 11, in particular in a transition region between the printed circuit board 352 and the sensing zone 12 or communication zone 14. In addition, the distance between the slits 364 is selected in accordance with the diameter of the inner and outer wraps 21, 22 in such a way that at least one slit 364 of the inner wrap 21 substantially overlaps with at least one slit 364 of the outer wrap 22. In this way, the at least two overlapping slits 364 of inner and outer wraps 21, 22 provide a recess in the side walls of inner and outer wraps 21, 22 thereby allowing visual inspection of the cartridge holder 304 and the cartridge 30. At least a sidewall portion 308 of the cartridge holder 304 is substantially transparent to provide visual inspection of the cartridge 30 and the contents of the cartridge 30. Due to the overlapping slits 364 in the foil 11, a substantially transparent foil is not required. Hence, the foil 11 can be made of a substantially non-transparent elastic material.

LIST OF REFERENCE NUMBERS 1 distal direction
2 proximal direction
3 top side
4 bottom side
5 integrated circuit
10 sensor
11 foil
12 sensing zone
13 transition zone
14 communication zone
15 recess
16 side edge
17 recess
18 side edge
19 boundary portion
20 sensor assembly
21 inner wrap
22 outer wrap
30 cartridge
32 barrel
34 liquid substance
35 seal
36 piston
38 closure
50 processor
51 antenna
52 conducting path
55 temperature sensor
60 capacity meter
61 electrode
62 electrode
68 gap
70 scale
80 electric shield
82 conductor
83 conductor
84 conductor
100 drug delivery device
102 housing
104 cartridge holder
106 socket
107 through opening
108 inspection window
110 dial
112 dose button
114 needle assembly
116 needle hub
118 injection needle
120 slit
130 drive mechanism
132 piston rod 160a,b,c capacity meter
161 electrode
162 electrode
163 electrode
164 electrode
165 electrode
166 electrode
167 gap
168 gap
261 electrode
262 electrode
263 electrode
264 electrode
265 electrode
266 electrode
267 gap
268 gap
300 sensor assembly
304 cartridge holder
305 fastening element
306 slit
308 sidewall portion
310 sensor
320 distal housing
321 sidewall
322 fastening element
323 fastening element
350 processor
351 antenna
352 printed circuit board
353 fastening structure
354 fastening structure
355 fastening element
361 electrode
362 electrode
364 slit

The invention claimed is:

1. A sensor for a capacitive determination of a filling level of a cartridge filled with a liquid substance, the sensor comprising:
a planar flexible foil arrangeable to an outer circumference of a tubular shaped barrel of the cartridge, the planar flexible foil having at least a sensing zone and a communication zone;
at least a first electrode and at least a second electrode implemented as electrical capacity measurement electrodes located in the sensing zone, and being permanently and fixedly attached to the flexible foil;
a processor electrically connected with the at least first electrode and the at least second electrode; and
an antenna located in the communication zone and electrically connected with the processor,
wherein the planar flexible foil is wrappable around the tubular shaped barrel of the cartridge and wherein the sensing zone and the communication zone are non-overlapping sections of the planar flexible foil.

2. The sensor according to claim 1, further comprising an electrical shield located in the communication zone and comprising at least two electrically isolated conductive structures.

3. The sensor according to claim 2, wherein the electrical shield and the antenna are electrically isolated and are located on opposite sides of the planar flexible foil.

4. The sensor according to claim 2, wherein the planar flexible foil is substantially transparent and wherein at least one of the at least first electrode or the at least second electrode, the antenna, and the electrical shield comprises a printed or coated conductive structure on or in the flexible planar foil.

5. The sensor according to claim 1, further comprising a visual scale in the communication zone.

6. The sensor according to claim 1, wherein the processor is located in a transition zone of the planar flexible foil that is located between the communication zone and the sensing zone.

7. The sensor according to claim 6, further comprising a temperature sensor in one of the communication zone, the transition zone, or the sensing zone.

8. The sensor according to claim 6, further comprising a visual scale in the communication zone and a temperature sensor in one of the communication zone, the transition zone or the sensing zone.

9. The sensor according to claim 6, wherein the transition zone comprises a narrowed neck portion formed by at least one lateral recess in a side edge of the planar flexible foil.

10. The sensor according to claim 1, wherein the processor is arranged on a rigid printed circuit board fixed to or integrated into the planar flexible foil.

11. A sensor assembly for a capacitive determination of a filling level of a cartridge, the sensor assembly comprising:
at least one of:
(i) a cartridge having a tubular shaped barrel and being filled with a liquid substance, and
(ii) a cartridge holder to accommodate the cartridge; and
a sensor comprising:
a planar flexible foil arrangeable to an outer circumference of the tubular shaped barrel of the cartridge, the foil having at least a sensing zone and a communication zone,
at least a first electrode and at least a second electrode implemented as electrical capacity measurement electrodes located in the sensing zone, and being permanently and fixedly attached to the flexible foil,
a processor electrically connected with the first and second electrodes, and
an antenna located in the communication zone and electrically connected with the processor,
wherein the flexible foil is wrapped to form an inner wrap and an outer wrap, the sensing zone is located in the inner wrap, and the communication zone is located in the outer wrap, and
wherein the sensor is attached to the cartridge or to the cartridge holder.

12. The sensor assembly according to claim 11, wherein the inner wrap is wrapped around the outer circumference of the barrel and the inner wrap is adhesively attached to the barrel.

13. The sensor assembly according to claim 11, wherein the cartridge holder has a longitudinal slit in a sidewall portion through which the foil extends.

14. The sensor assembly according to claim 11, wherein the inner wrap is arranged or attached to an inside of a sidewall portion of the cartridge holder.

15. The sensor assembly according to claim 11, wherein the processor of the sensor is arranged on a rigid printed circuit board fixed to or integrated into the planar flexible foil and the printed circuit board and the cartridge holder comprise mutually engageable fastening elements for a mutual fixing of sensor and cartridge holder.

16. A drug delivery device for setting and dispensing of a dose of a medicament, the drug delivery device comprising:

a housing to accommodate a drive mechanism and at least one of a cartridge filled with a liquid medicament and a cartridge holder to accommodate the cartridge, the drive mechanism including a piston rod displaceable in an axial distal direction to exert distally directed thrust to a piston of a cartridge; and a sensor assembly comprising:
  at least one of the cartridge and the cartridge holder;
  a planar flexible foil arrangeable to an outer circumference of a tubular shaped barrel of the cartridge, the foil having at least a sensing zone and a communication zone,
  at least a first electrode and at least a second electrode implemented as electrical capacity measurement electrodes located in the sensing zone, and being permanently and fixedly attached to the flexible foil,
  a processor electrically connected with the first and second electrodes, and
  an antenna located in the communication zone and electrically connected with the processor,
  wherein the flexible foil is wrapped to form an inner wrap and to form an outer wrap, the sensing zone is located in the inner wrap, and the communication zone is located in the outer wrap, and
  wherein the sensor is attached to the cartridge or to the cartridge holder.

17. The drug delivery device according to claim 16,
  wherein the processor of the sensor assembly is arranged on a rigid printed circuit board fixed to or integrated into the planar flexible foil,
  wherein the printed circuit board and the cartridge holder comprise mutually engageable fastening elements for a mutual fixing of sensor and cartridge holder, and
  wherein the drug delivery device comprises a distal housing to accommodate the sensor assembly, wherein the distal housing comprises at least one fastening element to engage with a corresponding fastening structure of the printed circuit board of the sensor assembly.

18. The sensor according to claim 1, wherein the at least first electrode and the at least second electrode are arranged geometrically radially opposed along an outer circumference of the tubular shaped barrel of the cartridge when the planar flexible foil is wrapped around the tubular shaped barrel of the cartridge.

19. The sensor according to claim 2, wherein the electrical shield, the at least first electrode, and the at least second electrode are arranged on a same side of the planar flexible foil.

* * * * *